US010278591B2

(12) United States Patent
Gil (10) Patent No.: US 10,278,591 B2
(45) Date of Patent: May 7, 2019

(54) BLOOD GLUCOSE MEASUREMENT METHOD AND APPARATUS USING MULTIPLE BODY SIGNALS

(71) Applicant: HUINNO CO., LTD., Seongnam, Gyeonggi-Do (KR)

(72) Inventor: Yeong Joon Gil, Busan (KR)

(73) Assignee: HUINNO CO., LTD., Seongnam (KR)

( * ) Notice: Subject to any disclaimer, the term of this patent is extended or adjusted under 35 U.S.C. 154(b) by 837 days.

(21) Appl. No.: 14/779,857

(22) PCT Filed: Apr. 29, 2015

(86) PCT No.: PCT/KR2015/004324
§ 371 (c)(1),
(2) Date: Sep. 24, 2015

(87) PCT Pub. No.: WO2015/167251
PCT Pub. Date: Nov. 5, 2015

(65) Prior Publication Data
US 2016/0157733 A1    Jun. 9, 2016

(30) Foreign Application Priority Data
Apr. 29, 2014  (KR) .................. 10-2014-0051420

(51) Int. Cl.
*A61B 5/1455*  (2006.01)
*A61B 5/0205*  (2006.01)
(Continued)

(52) U.S. Cl.
CPC .............. *A61B 5/0205* (2013.01); *A61B 5/01* (2013.01); *A61B 5/0245* (2013.01);
(Continued)

(58) Field of Classification Search
CPC ..... A61B 5/1455; A61B 5/14532; A61B 5/72; A61B 5/7225
See application file for complete search history.

(56) References Cited

U.S. PATENT DOCUMENTS 5,957,841 A * 9/1999 Maruo ............... A61B 5/14532
600/316

FOREIGN PATENT DOCUMENTS

JP        2008-035918 A    2/2008
KR    10-2003-0019927 A    3/2003
(Continued)

OTHER PUBLICATIONS

International Search Report issued in corresponding International Application No. PCT/KR2015004324 dated Aug. 11, 2015, 3 pages.

*Primary Examiner* — Eric F Winakur
(74) *Attorney, Agent, or Firm* — Mintz Levin Cohn Ferris Glovsky and Popeo, P.C.; Kongsik Kim; Derek E. Constantine (57) ABSTRACT

Blood glucose measurement methods and apparatuses are provided using multiple body signals. The methods and apparatuses are employed to estimate blood glucose in a noninvasive manner by using a change in the absorbance of glucose according to a blood glucose level and to correct the estimated blood glucose using different types of blood glucose measurement methods. The blood glucose measurement apparatus includes a main body worn on a human body, a first light source provided on an inner surface of the main body, a second light source provided on the inner surface of the main body, a light receiver configured to receive light from the first light source and the second light source, and a calculator configured to calculate a glucose level in blood based on an amount of light received by the light receiver and configured to measure blood glucose.

15 Claims, 8 Drawing Sheets

(51) Int. Cl.
    *A61B 5/0402*     (2006.01)
    *A61B 5/145*     (2006.01)
    *A61B 5/00*     (2006.01)
    *A61B 5/01*     (2006.01)
    *A61B 5/0245*     (2006.01)
    *A61B 5/0285*     (2006.01)
    *A61B 5/0456*     (2006.01)
    *A61B 5/053*     (2006.01)
    *A61B 5/08*     (2006.01)

(52) U.S. Cl.
    CPC .......... *A61B 5/0285* (2013.01); *A61B 5/0402* (2013.01); *A61B 5/0456* (2013.01); *A61B 5/0533* (2013.01); *A61B 5/0816* (2013.01); *A61B 5/1455* (2013.01); *A61B 5/14532* (2013.01); *A61B 5/14551* (2013.01); *A61B 5/6826* (2013.01); *A61B 5/7225* (2013.01)

(56) References Cited

FOREIGN PATENT DOCUMENTS

| | | |
|---|---|---|
| KR | 10-2004-0064618 A | 7/2004 |
| KR | 10-2005-0073854 A | 7/2005 |
| KR | 10-2013-0048470 A | 5/2013 |

* cited by examiner

BLOOD GLUCOSE MEASUREMENT METHOD AND APPARATUS USING MULTIPLE BODY SIGNALS

CROSS-REFERENCE TO RELATED APPLICATIONS

This application claims the benefit under 35 U.S.C. § 371 of International Application No. PCT/KR2015/004324, filed on Apr. 29, 2015, which claims priority to Korean Application No. 10-2014-0051420 filed on Apr. 29, 2014. All of these applications are incorporated by reference herein.

TECHNICAL FIELD

The present invention relates to real-time blood glucose measurement using multiple body signals and to blood glucose measurement methods and apparatuses using multiple body signals.

BACKGROUND

Diabetes is a disease in which sugar accumulates in the blood of a patient because a hormone called insulin is not secreted enough by the pancreas or fails to work properly. Diabetes causes various complications, including high blood pressure, kidney failure, and damage to the eyes. Because there is no complete treatment for diabetes, a patient must maintain an appropriate glucose level in his or her blood through dietary treatment, exercise treatment, and the injection of insulin. For the management of blood glucose levels, accurately measuring blood glucose is essential.

To measure blood glucose levels, many methods exist, such as a method based on the reducibility of glucose, a method using a direct reaction of sugar in an acid condition, and a method using an enzymatic reaction of glucose. In addition, methods used in clinical medicine include a method in which blood drawn from a finger or a toe is made to react with glucose oxidase, the degree of coloring is measured by utilizing a coloring reaction dependent on the concentration of glucose in blood, and the measured degree of coloring is converted into a blood glucose level. However, these invasive blood sugar measurement methods require diabetic patients to endure the pain of blood extraction. Blood extraction is required multiple times a day and puts the diabetic patients at risk of additional problems, such as infection.

Accordingly, an electrochemical method is widely used to measure blood glucose. In this method, blood is drawn and made to react with an enzyme. A blood glucose level is then measured by measuring the amount of current flowing in response to a predetermined voltage applied to the blood. However, this method requires not only the pain of blood extraction for each measurement but also continually purchasing disposable strips for blood glucose measurement.

Many noninvasive blood glucose measurement techniques have been used. These techniques measure blood glucose levels by irradiating infrared light to the skin and then analyzing the degree of infrared light absorbed or scattered in the skin. However, measured blood glucose levels in this method may vary widely according to a number of different factors unrelated to a patient's glucose level, such as the measurement location on the skin, the temperature of the skin, etc. These techniques are thus not widely used.

There is therefore a need for noninvasive blood glucose measurements that accurately measure blood glucose levels despite varying environments.

SUMMARY

The present invention relates to addressing problems in conventional blood pressure monitoring systems. Provided herein is a blood glucose measurement method and apparatus using multiple body signals. The method and apparatus may be capable of continuously monitoring blood glucose levels in a noninvasive manner by using a blood glucose sensor provided in a main body wearable on a human body.

Also provided herein is a blood glucose measurement method and apparatus using multiple body signals. The method and apparatus may be capable of measuring blood glucose levels by measuring the degree of light absorbed in a human body from among light irradiated from a light source provided in a main body wearable on the human body.

Additionally provided herein is a blood glucose measurement method and apparatus using multiple body signals. The method and apparatus may be capable of measuring blood glucose levels by detecting body signals, such as electrocardiogram (ECG), photoplethysmography (PPG), saturation of peripheral oxygen ($SpO_2$), galvanic skin reflex (GSR), body temperature, and breathing pattern, and using the detected body signals as auxiliary information.

However, the objectives of the present invention are not restricted to the one set forth herein. The above and other objectives of the present invention will become more apparent to one of ordinary skill in the art to which the present invention pertains by referencing a detailed description of the present invention given below.

According to an aspect of the present invention, an exemplary embodiment is provided including a blood glucose measurement apparatus using multiple body signals. The apparatus may include a main body that may be worn on a human body. The apparatus may also include a first light source that may be provided on an inner surface of the main body and may contact the human body wearing the main body. The apparatus may additionally include a second light source that may be provided on the inner surface of the main body and may irradiate light in the same direction as the first light source. The apparatus may include a light receiver that may receive light from the first light source and the second light source and a calculator that may calculate a glucose level in blood based on the amount of light received by the light receiver and may measure blood glucose using the calculated glucose level in the blood.

The first light source may irradiate light having a wavelength of about 1850 to 1920 nm, and the second light source unit may irradiate light having a wavelength of about 2050 to 2130 nm.

The main body may have a groove or an aperture, into which a finger or a wrist can be inserted, on a side thereof.

The calculator may calculate the glucose level in the blood using BloodGlucose=$(X_{t_1} \times P1)+(Y_{t_2} \times P2)+P3$ by combining the amount of light X of the first light source received at a time a predetermined period of time t1 before a current time and the amount of light Y of the second light source received at a time a predetermined period of time t2 before the current time with unique constants P1, P2 and P3.

The light receiver may include a light receiving sensor that receives light irradiated from the first light source or the second light source, a timing circuit that classifies an optical signal received by the light receiving sensor according to wavelength, a current-voltage converter that converts a current signal output from the light receiving sensor into a voltage signal, a first operational amplifier that amplifies a signal output from the current-voltage converter, a high-pass filter that passes a signal of about 0.1 Hz or higher from among signals that passed through the first operational amplifier, a low-pass filter that passes a signal of about 20 Hz or lower from among the signals that passed through the first operational amplifier, and a second operational amplifier that amplifies a signal that passed through the high-pass filter and the low-pass filter.

The apparatus may further include a body information detector that is provided on the inner surface of the main body to contact the human body and may be configured to measure any one of electrocardiogram (ECG) and photoplethysmography (PPG). The calculator may correct the calculated glucose level in the blood using a value detected by the body information detector. The apparatus may further include a body information detector that is provided on the inner surface of the main body to contact the human body and may be configured to measure any one of saturation of peripheral oxygen (SpO₂) and PPG. The calculator may correct the calculated glucose level in the blood using a value detected by the body information detector. The apparatus may further include a body information detector that is provided on the inner surface of the main body to contact the human body and may be configured to measure any one of galvanic skin reflex (GSR) and body temperature. The calculator may correct the calculated glucose level in the blood using a value detected by the body information detector.

The apparatus may further include a breathing pattern detector on an outer surface of the main body and that may be configured to measure a breathing pattern when placed adjacent to a respiratory system. The calculator may correct the calculated glucose level in the blood using a value detected by the breathing pattern detector.

A blood glucose measurement method and apparatus using multiple body signals related to the present invention may provide advantages. Because the same amount of light is absorbed by water from among light of a wavelength irradiated from a first light source and light of a wavelength irradiated from a second light source, a blood glucose level may be accurately measured by excluding the amount of light absorbed by water.

Because the same amount of light is lost by water from among light irradiated from the first light source and light irradiated from the second light source, a difference in the amount of light received by a light receiver may be purely attributable to a difference in blood glucose level. Therefore, a blood glucose level may be negligibly affected by measurement location or body temperature. Because the blood glucose measurement apparatus may be wearable on a human body such as a wrist or a finger, a blood glucose level of a subject wearing the blood glucose measurement apparatus may be continuously monitored. Therefore, a sudden change in blood glucose level may be dealt with.

A glucose level at the time of measurement may not be used to calculate a glucose level. Instead, the glucose level may be calculated based on a glucose value before a blood glucose level has been changed by the external environment. Therefore, an accurate blood glucose measurement may be possible. A blood glucose level measured by calculating a glucose level may be corrected using a body signal such as electrocardiogram (ECG) or photoplethysmography (PPG). Therefore, an accurate blood glucose level may be identified.

A blood glucose level measured by calculating a glucose level may be corrected using a body signal such as saturation of peripheral oxygen (SpO₂) or PPG. Therefore, an accurate blood glucose level may be identified. A blood glucose level measured by calculating a glucose level may be corrected using a body signal such as galvanic skin reflex (GSR) or body temperature. Therefore, an accurate blood glucose level may be identified.

A blood glucose level measured by calculating a glucose level may be corrected using a body signal such as a breathing pattern. Therefore, an accurate blood glucose level may be identified. However, the effects of the present invention are not restricted to any one set forth herein. The above and other effects of the present invention will become more apparent to one of ordinary skill in the art to which the present invention pertains by referencing the claims.

DESCRIPTION OF DRAWINGS

The above and other aspects and features of the present invention will become more apparent by describing in detail exemplary embodiments thereof with reference to the attached drawings, in which.

DETAILED DISCLOSURE

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Although exemplary embodiments may be described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Hereinafter, exemplary embodiments of the present invention will be described in further detail with reference to the attached drawings.

A blood glucose measurement principle related to the present invention is to measure a blood glucose level based on the amount of light absorbed in a human body from among light irradiated to the human body. More specifically, water exists not only in blood but also in bones and cortical layers of the human body. Therefore, water is inappropriate to be used as a parameter. A blood glucose level may thus be detected not by measuring mixed light of two or more water-containing materials with different absorbances. Instead, because the concentration of glucose in blood varies according to the blood glucose level, the absorbance of only glucose may be used to detect glucose content in blood.

Figure 1:
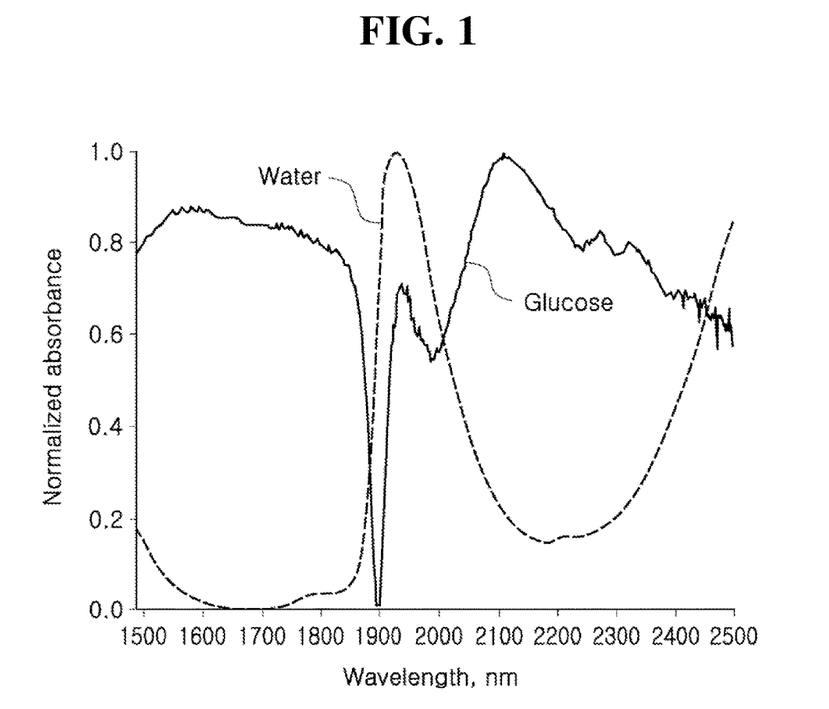
FIG. 1 is a graph illustrating optical wavelength versus absorbance to explain a blood glucose measurement principle of an exemplary embodiment of the present invention.

Referring to FIG. 1, water has the same absorbance of about 30% for light having a wavelength of about 1880 nm and light having a wavelength of about 2080 nm. On the other hand, glucose has different absorbance values for the light having the above wavelengths. While glucose, like water, absorbs about 30% of the light having the wavelength of about 1880 nm, it absorbs about 90% of the light having the wavelength of about 2080 nm. Therefore, if the light having the wavelength of about 1880 nm and the light having the wavelength of about 2080 nm are alternately irradiated to the same location on the human body, the lights may transmit through the human body to be received in different amounts. This difference in the amount of light received may thus result from a difference in the absorbance of glucose.

Figure 2:
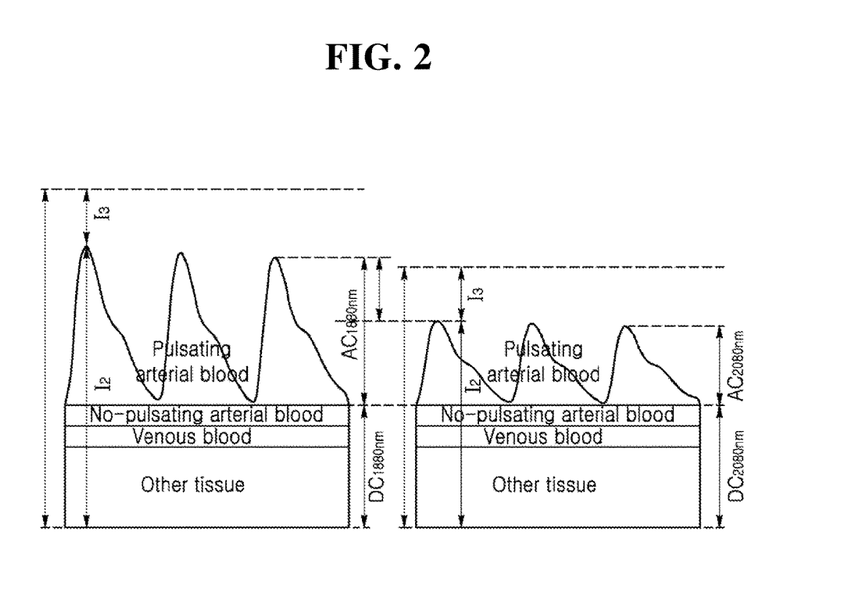
FIG. 2 is a graph illustrating optical wavelengths detected in response to the irradiation of light having a wavelength of about 1880 nm and light having a wavelength of about 2080 nm.

After each of the light having the wavelength of about 1880 nm and the light having the wavelength of about 2080 nm is irradiated to the same location on the human body and light that passed through the human body is received, the results as shown in FIG. 2 can be obtained. The received optical signal of each wavelength is divided into an alternating current (AC) component and a direct current (DC) component. Here, the AC component indicates the amount of light absorbed by blood passing through peripheral blood vessels, and the DC component indicates the amount of light absorbed by capillaries or tissue such as muscles, epidermis and bones.

Because water has the same absorbance of about 30% for both the light having the wavelength of about 1880 nm and the light having the wavelength of about 2080 nm, the amount of light lost by water from among the amount of light lost as light irradiated from a light source passes through the human body may be the same for both of the lights for the two wavelengths. Therefore, the DC components of the received signals may be presented as illustrated in the drawing based on an analysis of the received signals.

On the other hand, glucose has far higher absorbance than water for the light having the wavelength of 2080 nm. As a blood glucose level increases, therefore, the amplitude of the AC component detected is smaller than that for the light having the wavelength of 1880 nm. Based on the amounts of light detected for the above two wavelengths, a model for estimating a blood glucose level can be established as follows.

$$\text{Blood Glucose} = (X_t 1 \times P1) + (Y_t 2 \times P2) + P3, \quad (1)$$

where X is the amount of light received from among the light having the wavelength of about 1880 nm, and Y is the amount of light received from among the light having the wavelength of about 2080 nm.

In addition, t1 and t2 are predetermined periods of time before a current time when a blood glucose level is measured. The amounts of light X and Y measured during the predetermined periods of time t1 and t2 before the current time are used to measure a blood glucose level because it takes approximately 20 to 30 seconds for blood released from the heart to return to the heart and because it takes time for a stimulus, such as meal intake, exercise, or insulin secretion, to affect glucose in blood. Therefore, to detect a blood glucose level before the blood glucose level is changed by a stimulus, the amounts of light X and Y measured during the periods of time t1 and t2 before the current time are used. The periods of time t1 and t2 may be variables that can be set directly by a subject or set automatically by a system that executes blood glucose measurement based on the situation and the environment in which blood glucose measurement is needed.

Figure 3:
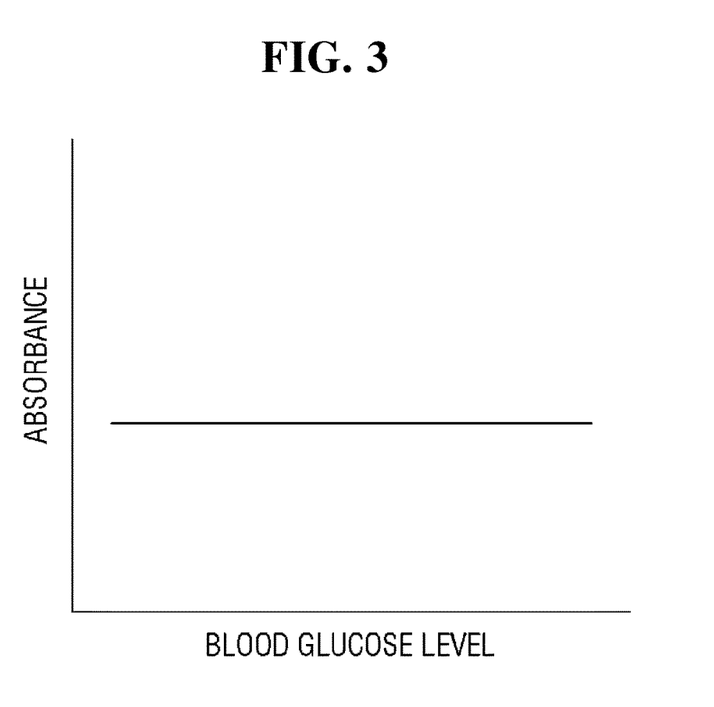
FIG. 3 is a graph illustrating a subject's blood glucose level versus absorbance in response to light having a wavelength of about 1880 nm.
Figure 4:
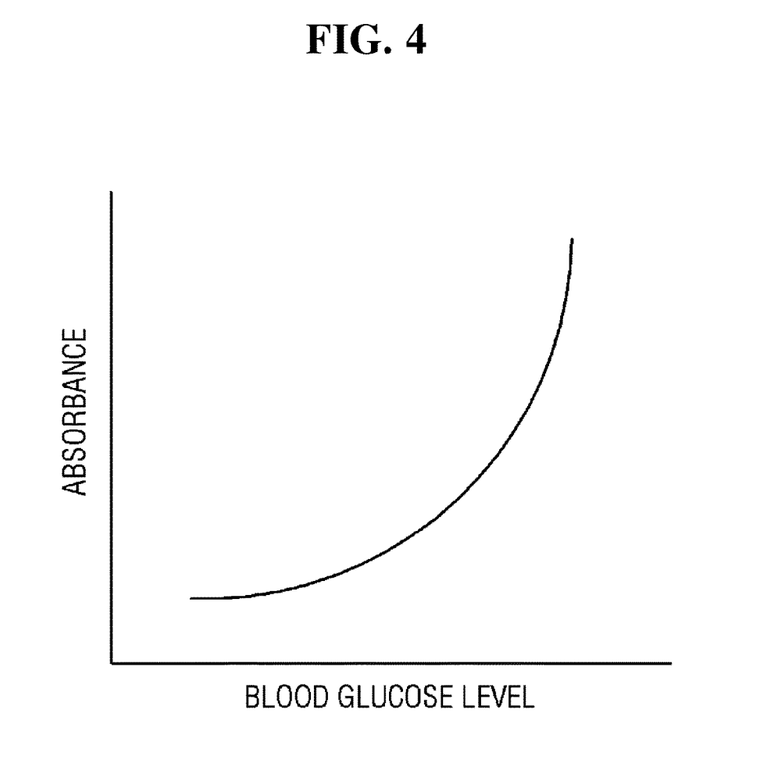
FIG. 4 is a graph illustrating a subject's blood glucose level versus absorbance in response to light having a wavelength of about 2080 nm.

Further, P1, P2, and P3 are constants used to calculate a glucose level based on the amounts of light received and may be defined through statistical analysis or mathematical modeling. FIG. 3 is a graph illustrating a subject's blood glucose level versus absorbance in response to light having a wavelength of about 1880 nm, and FIG. 4 is a graph illustrating a subject's blood glucose level versus absorbance in response to light having a wavelength of about 2080 nm. Referring to FIG. 3, the absorbance of glucose for the light having the wavelength of about 1880 nm remains constant regardless of whether a blood glucose level is high or low.

Referring to FIG. 4, the absorbance of glucose for the light having the wavelength of about 2080 nm increases in proportion to an increase in blood glucose level. The proportion of glucose in the blood of a subject with a high blood glucose level is greater than a proportion with a normal level. Therefore, the amount of light received after the light having the wavelength of about 1880 nm is irradiated to the body of the subject with a high blood glucose level is not much different than the amount of light received after the light having the wavelength of about 1880 nm is irradiated to the body of a subject with a normal blood glucose level. However, the amount of light received after the light having the wavelength of about 2080 nm is irradiated to the body of the subject with a high blood glucose level is less than the amount of light received after the light having the wavelength of about 2080 nm is irradiated to the body of the subject with a normal blood glucose level.

In this regard, the amount of light received after the irradiation of the light having the wavelength of about 1880 nm can be used as a basis for identifying the absorbance of water in the body of a subject whose blood glucose level is measured. In addition, the amount of light received after the irradiation of the light having the wavelength of about 2080 nm can be used as a value for detecting whether a blood glucose level is higher or lower than that calculated based on the amount of light received after the irradiation of the light having the wavelength of about 1880 nm.

Figure 5:
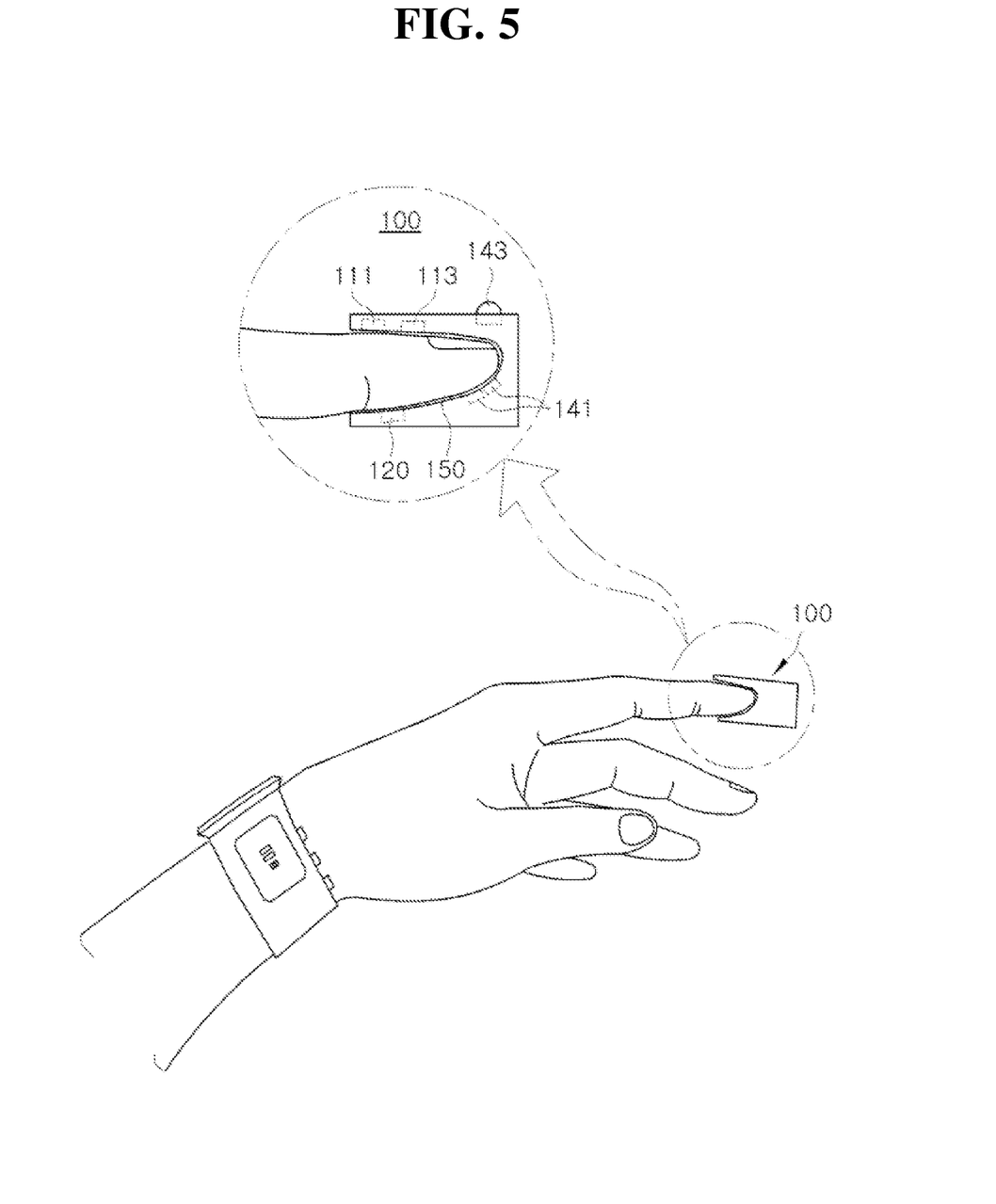
FIG. 5 is a cross-sectional view of a blood glucose measurement method and apparatus using multiple body signals according to an exemplary embodiment of the present invention.
Figure 6:
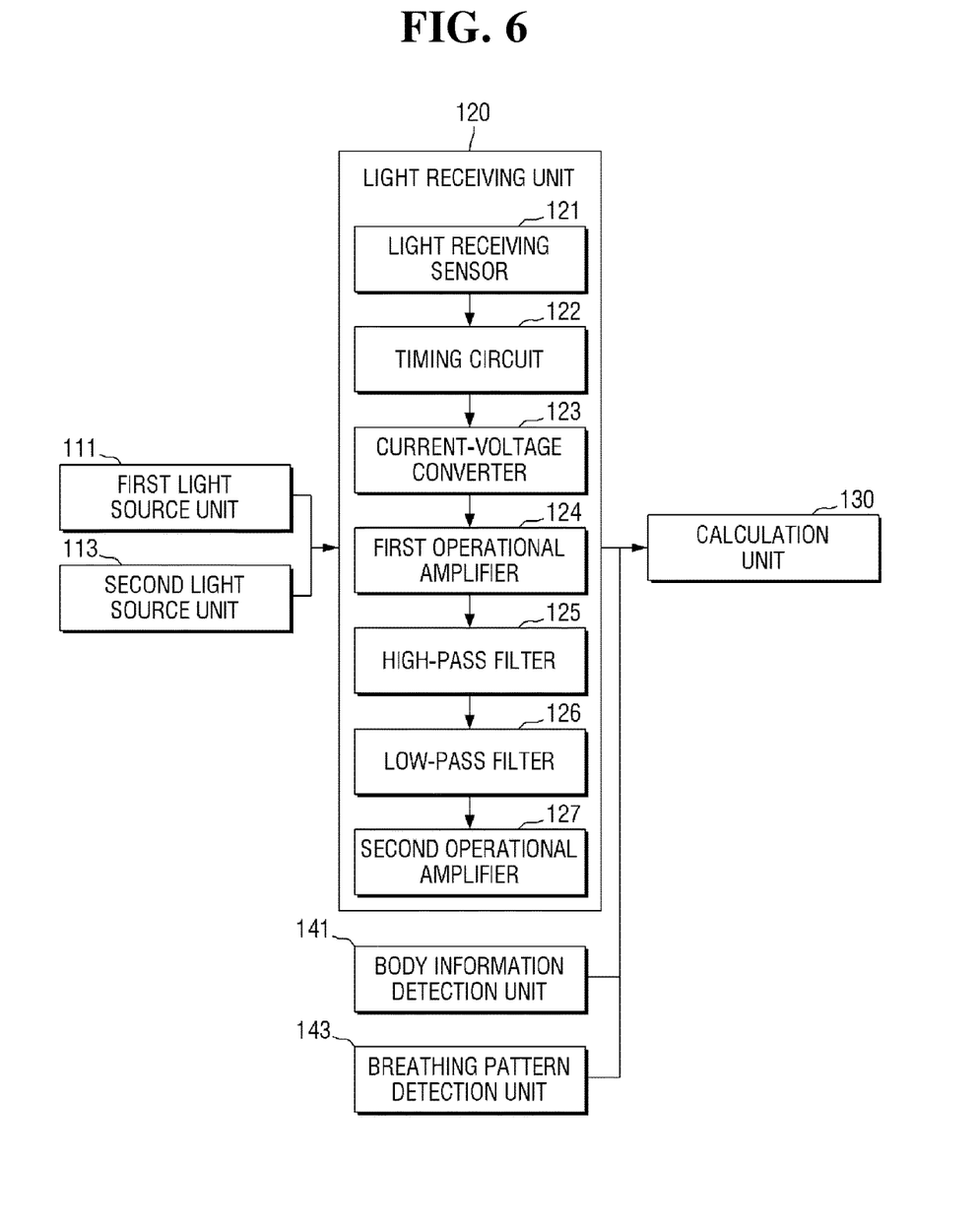
FIG. 6 illustrates the configuration of the blood glucose measurement method and apparatus of FIG. 5.

A blood glucose measurement method and apparatus using multiple body signals and based on the above blood glucose measurement theory related to an exemplary embodiment of the present invention will hereinafter be described. FIG. 5 is a cross-sectional view of a blood glucose measurement method and apparatus using multiple body signals. FIG. 6 illustrates the configuration of the blood glucose measurement method and apparatus of FIG. 5. Referring to FIGS. 5 and 6, the blood glucose measurement apparatus using multiple body signals according to the current exemplary embodiment may include a main body 100 that may be worn on a human body. The apparatus may also include a first light source 111 that may be provided on an inner surface of the main body 100 and may contact the human body wearing the main body 100. A second light source 113 may also be included that may be on the inner surface of the main body 100 and may irradiate light in the same direction as the first light source 111. The apparatus may also include a light receiver 120 that receives light from the first light source 111 and the second light source 113 and a calculator 130 that may calculate a glucose level in blood based on the amount of light received by the light receiver 120 and may measure blood glucose using the calculated glucose level. Light sources, receivers, calculators, and/or any units may be operated by a controller having a memory and a processor.

The main body 100 may have a shape that allows it to be worn on a human body. For example, the main body 100 may be shaped like a bracelet having an aperture so as to be worn on the wrist or, as in the current exemplary embodiment, shaped like a thimble having a groove 150 into which a finger may be inserted. In addition, to receive light irradiated from the first light source 111 and the second light source 113, the light receiver 120 may be provided inside the main body 100 at a location facing the first light source 111 and the second light source 113.

The first light source 111 may irradiate light having a wavelength of about 1850 to 1920 nm, and the second light source 113 may irradiate light having a wavelength of about 2050 to 2130 nm. The light having the wavelength of about 1850 to 2130 nm is light in an infrared wavelength region and cannot be perceived by human eyes. The first light source 111 may have the wavelength of about 1850 to 1920 nm because glucose and water have similar absorbance values in the above wavelength region. Therefore, the first light source 111 can be used to measure the absorbance of water in the body of a subject and identify body characteristics of the subject so as to measure blood glucose.

In addition, the second light source 113 may have the wavelength of about 2050 to 2130 nm because the absorbance of water in the above wavelength region is similar to that in the wavelength region of the first light source 111. Therefore, the absorbance of water can be identified using the second light source 113. On the other hand, because the absorbance of glucose is higher in the wavelength region of the second light source 113 than in the wavelength region of the first light source 111, a glucose level can be inferred using this difference.

When light irradiated from the first light source 111 and the second light source 113 is received by the light receiver 120, the calculator 130 may calculate a blood glucose level using Equation (1) by combining the amount of light X of the first light source 111 received at a predetermined period of time t1 before a current time and the amount of light Y of the second light source 113 received at a predetermined period of time t2 before the current time with unique constants P1, P2, and P3 used to measure a glucose level in blood.

Figure 7:
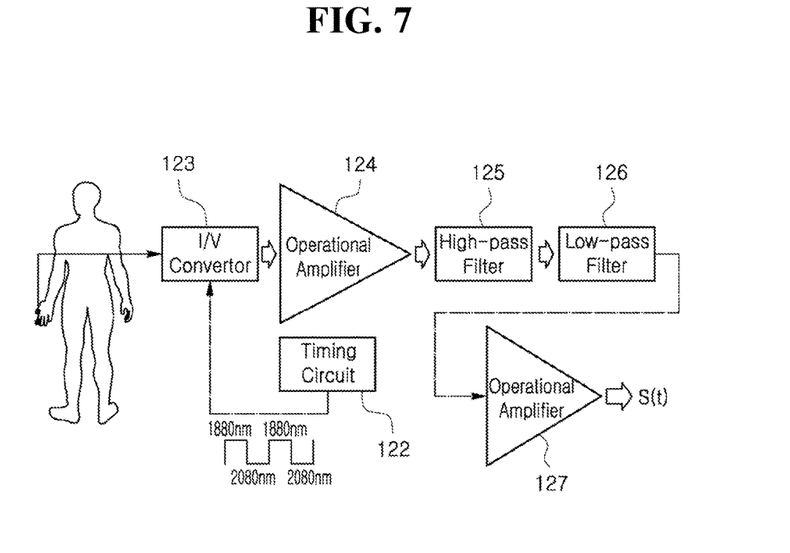
FIG. 7 illustrates the detailed configuration of a light receiver according to an exemplary embodiment of the present invention.

Referring to FIG. 7, the light receiver 120 may include a light receiving sensor 121 that receives light irradiated from the first light source 111 or the second light source 113. The light receiver 120 may also include a timing circuit 122 that classifies an optical signal received by the light receiving sensor 121 according to wavelength and a current (I)-voltage (V) converter 123 that converts a current signal output from the light receiving sensor 121 into a voltage signal. The light receiver 120 may additionally include a first operational amplifier 124 that amplifies a signal output from the I-V converter 123, a high-pass filter 125 that passes a signal of 0.1 Hz or higher from among signals that passed through the first operational amplifier 124, a low-pass filter 126 that passes a signal of 20 Hz or lower from among the signals that passed through the first operational amplifier 124, and a second operational amplifier 127 that amplifies a signal that passed through the high-pass filter 125 and the low-pass filter 126.

A signal that passed through the timing circuit 122 may be amplified by the first operational amplifier 124 such that a voltage gain of the signal becomes ten times. The amplified signal may pass through the high-pass filter 125 that passes a signal of 0.1 Hz or higher and the low-pass filter 126 that passes a signal of 20 Hz or lower. Then, the signal may be amplified again by the second operational amplifier 127 such that the voltage gain of the signal becomes 50 times. Ultimately, the voltage gain of the signal that passes through the timing circuit 122 may be amplified 500 times to 25 dB.

In addition, to minimize an error in a glucose level calculated by the calculator 130, the calculated glucose level may be corrected using a blood glucose level obtained by detecting different types of body information. For example, a body information detector 141 that measures any one of electrocardiogram (ECG) and photoplethysmography (PPG) may further be provided on the inner surface of the main body 100 to contact the human body, and the calculator 130 may correct the calculated glucose level using a value detected by the body information detector 141. An ECG is a waveform that represents the vector sum of action potentials generated by a special excitatory and conductive system. The ECG is thus a vector sum signal, measured using electrodes attached onto the human body, of action potentials generated by each component of the heart, such as sinoatrial (SA) node, atrioventricular (AV) node, His bundle, bundle branches, Purkinje fibers, etc.

An ECG signal may be obtained using a limb lead method that utilizes four electrodes. A PPG is a pulse wave signal measured in peripheral blood vessels when blood ejected during ventricular systole is delivered to the peripheral blood vessels. To measure a PPG signal, optical characteristics of biological tissue may be used. Pulse transit time (PTT) or pulse wave velocity (PWV) may be extracted by analyzing the correlation between a PPG signal and an ECG signal, instead of only the PPG signal, and cardiovascular diseases may be diagnosed based on the extracted PTT and/or PWV. A characteristic point may thus be obtained by performing a quadratic differential on the PPG signal, and then a time interval from a peak (R wave) of the ECG signal may be measured.

A reduction of glucose in blood increases a heart rate in a patient to supply more blood, and an ECG changes according to a change in blood glucose. For example, a reduction in an R-R interval value in an ECG waveform may increase the heart rate. Therefore, the reduction in the R-R interval value may be interpreted as representing a fall in blood glucose level. In addition, a high frequency (HF)/low frequency (LF) ratio, which represents a change in ECG, and a change in the time range of a QRST waveform may also vary according to a change in blood glucose level. Therefore, these body signals and the R-R interval may be used as constants that are proportional to a blood glucose level in order to increase the accuracy of measured blood glucose levels.

In addition, the body information detector 141 that measures saturation of peripheral oxygen ($SpO_2$) and/or PPG may further be provided on the inner surface of the main body 100 to contact the human body, and the calculator 130 may correct the calculated glucose level using a value detected by the body information detector 141. $SpO_2$ is a body signal indicating oxygen content in hemoglobin from among various components of blood. A lack of insulin in the human body may increase the heart rate, thus lowering a $SpO_2$ value and changing a breathing cycle.

A body information detector 141 that measures any one of galvanic skin reflex (GSR) and body temperature may further be provided on the inner surface of the main body 100 to contact the human body, and the calculator 130 may correct the calculated glucose level using a value detected by the body information detector 141. GSR is a body signal measurement method that may be used to measure the psychological and physical arousal state of a subject based on the electrical conductivity of the skin because sweat glands of the skin are under the control of the subject's sympathetic nervous system.

A drop in blood glucose may increase the heart rate, causing cold sweating. Cold sweating is a phenomenon that occurs when contraction and dilatation of the heart are caused not by an external stimulus but by a hormone imbalance due to a lack of insulin. Such a change in the human body causes a change in GSR. Therefore, if the change in GSR is measured, a value proportional to a blood glucose level can be obtained. Body temperature falls as blood glucose falls. Therefore, if a fall in body temperature is detected, the fall may be interpreted as a fall in blood glucose. Thus body temperature may be used to measure blood glucose.

A breathing pattern detection unit 143 that measures a breathing pattern when placed adjacent to a respiratory system may further be provided on an outer surface of the main body 100, and the calculator 130 may correct the calculated glucose level using a value detected by the breathing pattern detector 143. A lack of insulin in the human body may increase the heart rate, thus lowering the $SpO_2$ value and increasing the breathing cycle. Therefore, if the main body 100 is placed adjacent to the respiratory system during blood glucose measurement, a breathing pattern of a subject may be measured by the breathing pattern detector 143 provided on the outer surface of the main body 100. The detected breathing pattern may therefore be used as an auxiliary means of inferring blood glucose.

Figure 8:
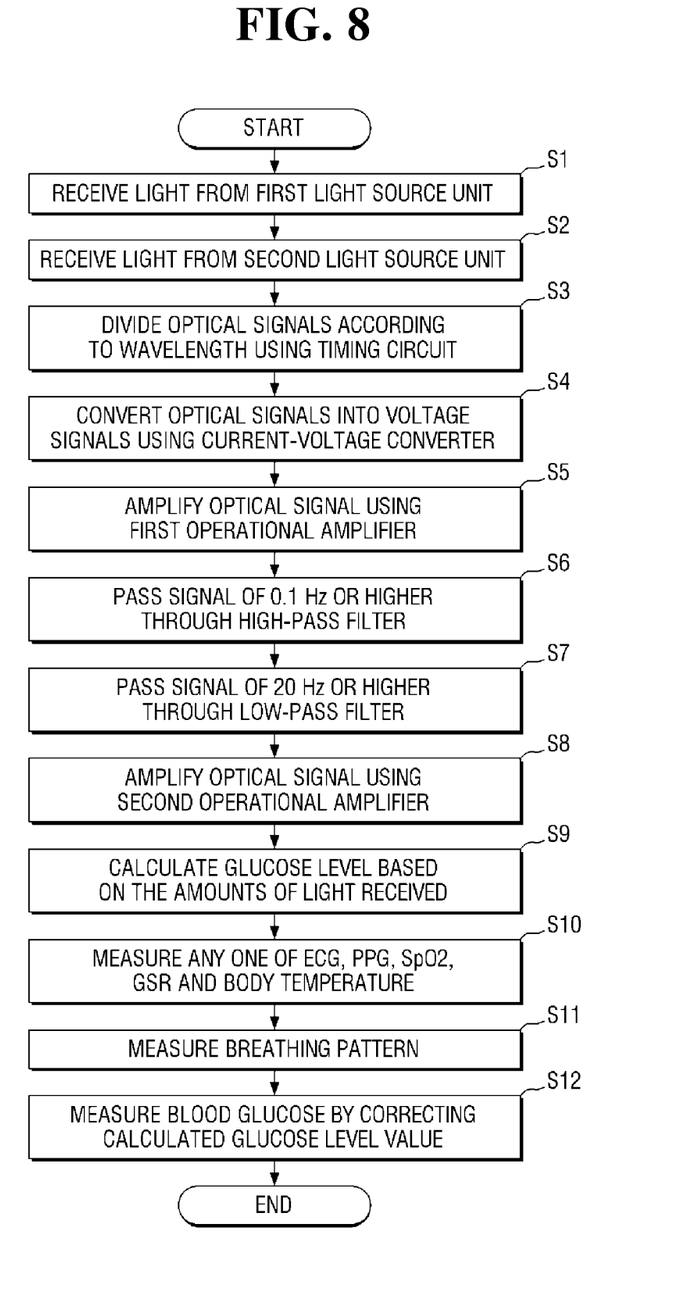
FIG. 8 is a flowchart illustrating a process of measuring blood glucose according to an exemplary embodiment of the present invention.

Hereinafter, a method of measuring blood glucose by utilizing a blood glucose measurement apparatus using multiple body signals related to an exemplary embodiment will be described. FIG. 8 is a flowchart illustrating a process of measuring blood glucose according to an exemplary embodiment. The method may include receiving first light having a wavelength of about 1850 to 1920 nm from a first light source 111 by using a light receiver 120 (operation S01), receiving second light having a wavelength of about 2050 to 2130 nm from a second light source 113 by using the light receiver 120 (operation S02), and calculating a glucose level in blood based on the amounts of the first light and the second light received by the light receiver 120 and measuring blood glucose based on the calculated glucose level by using a calculator 130 (operation S09).

In addition, the method may further include, after receiving of the first light and the second light using the light receiver 120 (operations S01 and S02), dividing the received optical signals into the first light and the second light using a timing circuit 122 (operation S03) and converting the optical signals divided into the first light and the second light by the timing circuit 122 into voltage signals using an I-V converter 123 (operation S04). The method may also include amplifying a signal output from the I-V converter 123 using a first operational amplifier 124 (operation S05), passing a signal of 0.1 Hz or higher through a high-pass filter 125 from among signals that passed through the first operational amplifier 124 (operation S06), passing a signal of 20 Hz or lower through a low-pass filter 126 from among the signals that passed through the first operational amplifier 124 (operation S07), and amplifying a signal that passed through the high-pass filter 125 and the low-pass filter 126 using a second operational amplifier 127 (operation S08).

The calculator 130 may also calculate the glucose level after excluding about 20 to 40% of light absorbed and thus lost by water in a human body from the amount of light received by the light receiver 120. In addition, the calculator 130 may calculate the glucose level in the blood as in Equation (1) by combining the amount of light X of the first light source 111 received at a predetermined period of time t1 before a current time and the amount of light Y of the second light source 113 received at a predetermined period of time t2 before the current time with unique constants P1, P2, and P3 used to measure the glucose level in the blood.

The method may further include, after calculating the glucose level in the blood using the calculator 130, measuring ECG and/or PPG using a body information detector 141 (operation S10) and correcting the glucose level in the blood calculated by the calculator 130 with a value detected by the body information detector 141 (operation S12). In addition, the method may further include, after calculating the glucose level in the blood using the calculator 130, measuring $SpO_2$ and/or PPG using a body information detector 141 (operation S10) and correcting the glucose level in the blood calculated by the calculator 130 using a value detected by the body information detector 141 (operation S12).

The method may additionally include, after calculating the glucose level in the blood using the calculator 130, measuring GSR and/or body temperature using a body information detector 141 (operation S10) and correcting the glucose level in the blood calculated by the calculator 130 using a value detected by the body information detector 141 (operation S12). In addition, the method may further include, after calculating the glucose level in the blood using the calculator 130, measuring a breathing pattern using a breathing pattern detector 143 (operation S11) and correcting the glucose level in the blood calculated by the calculator 130 using a value detected by the breathing pattern detector 143 (operation S12).

Although exemplary embodiments of the present invention have been described, the present invention may employ various modifications, changes, and equivalents. It will be apparent that the present invention may be equally applied by appropriately modifying the exemplary embodiments provided herein. Accordingly, the descriptions are not intended to limit the scope of the present invention defined by the appended claims.

The invention claimed is:

1. A blood glucose measurement apparatus using multiple body signals from a human body, the apparatus comprising:
   a main body configured to be worn on the human body;
   a first light source provided on an inner surface of the main body and arranged for contacting the human body wearing the main body;
   a second light source provided on the inner surface of the main body and configured to irradiate light in a same direction as the first light source;
   a light receiver configured to receive light from the first light source and the second light source, the light receiver including:
      a light receiving sensor configured to receive light irradiated from the first light source or the second light source,
      a timing circuit configured to classify an optical signal received by the light receiving sensor according to wavelength,
      a current-voltage converter configured to convert a current signal output from the light receiving sensor into a voltage signal,
      a first operational amplifier configured to amplify a signal output from the current-voltage converter,
      a high-pass filter configured to pass a signal of about 0.1 Hz or higher from among signals that passed through the first operational amplifier,
      a low-pass filter configured to pass a signal of about 20 Hz or lower from among the signals that passed through the first operational amplifier, and
      a second operational amplifier configured to amplify a signal that passed through the high-pass filter and the low-pass filter; and
   a calculator configured to calculate a glucose level in blood based on an amount of light received by the light receiver and configured to measure blood glucose using the calculated glucose level in the blood,
   wherein the calculator is configured to calculate the glucose level in the blood using BloodGlucose=$(X_t 1 \times P1)+(Y_t 2 \times P2)+P3$ by combining an amount of light X of the first light source received at a predetermined period of time t1 before a current time and an amount of light Y of the second light source received at a predetermined period of time t2 before the current time with unique constants P1, P2, and P3.

2. The apparatus of claim 1, wherein the first light source is configured to irradiate light having a wavelength of about 1850 to 1920 nm, and the second light source is configured to irradiate light having a wavelength of about 2050 to 2130 nm.

3. The apparatus of claim 1, wherein the main body has a groove or an aperture configured to receive a finger or a wrist and located on a side of the main body.

4. The apparatus of claim 1, further comprising:
   a body information detector (i) provided on the inner surface of the main body and arranged for contacting the human body and (ii) configured to measure any one of electrocardiogram (ECG) and photoplethysmography (PPG),
   wherein the calculator is configured to correct the calculated glucose level in the blood using a value detected by the body information detector.

5. The apparatus of claim 1, further comprising:
   a body information detector (i) provided on the inner surface of the main body and arranged for contacting the human body and (ii) configured to measure any one of saturation of peripheral oxygen (SpO$_2$) and PPG,
   wherein the calculator is configured to correct the calculated glucose level in the blood using a value detected by the body information detector.

6. The apparatus of claim 1, further comprising:
   a body information detector (i) provided on the inner surface of the main body and arranged for contacting the human body and (ii) configured to measure any one of galvanic skin reflex (GSR) and body temperature,
   wherein the calculator is configured to correct the calculated glucose level in the blood using a value detected by the body information detector.

7. The apparatus of claim 1, further comprising:
   a breathing pattern detector provided on an outer surface of the main body and configured to measure a breathing pattern when placed adjacent to a respiratory system,
   wherein the calculator is configured to correct the calculated glucose level in the blood using a value detected by the breathing pattern detector.

8. A blood glucose measurement apparatus using multiple body signals from a human body, the apparatus comprising:
   a main body having a groove or aperture sized to receive a finger or a wrist;
   a first light source (i) provided on an inner surface of the main body and arranged for contacting the human body wearing the main body and (ii) configured to irradiate light having a wavelength of about 1850 to 1920 nm;
   a second light source provided on the inner surface of the main body and configured to irradiate light having a wavelength of about 2050 to 2130 nm in a same direction as the first light source;
   a light receiver configured to receive light from the first light source and the second light source;
   a body information detector (i) provided on the inner surface of the main body and arranged for contacting the human body and (ii) configured to measure any one of ECG, PPG, SpO$_2$, GSR, and body temperature;
   a breathing pattern detector provided on an outer surface of the main body and configured to measure a breathing pattern when placed adjacent to a respiratory system; and
   a calculator configured to measure blood glucose by calculating a glucose level in blood using BloodGlucose=$(X_t 1 \times P1)+(Y_t 2 \times P2)+P3$ by combining an amount of light X of the first light source received at a predetermined period of time t1 before a current time and an amount of light Y of the second light source received at a predetermined period of time t2 before the current time with unique constants P1, P2, and P3,
   wherein the calculator is configured to correct the calculated glucose level in the blood using values detected by the body information detector unit and the breathing pattern detector, and
   wherein the light receiver includes:
      a light receiving sensor configured to receive light irradiated from the first light source or the second light source,
      a timing circuit configured to classify an optical signal received by the light receiving sensor according to wavelength,
      a current-voltage converter configured to convert a current signal output from the light receiving sensor into a voltage signal,
      a first operational amplifier configured to amplify a signal output from the current-voltage converter,
      a high-pass filter configured to pass a signal of about 0.1 Hz or higher from among signals that passed through the first operational amplifier, a low-pass filter configured to pass a signal of about 20 Hz or lower from among the signals that passed through the first operational amplifier, and a second operational amplifier configured to amplify a signal that passed through the high-pass filter and the low-pass filter.

9. A blood glucose measurement method using multiple body signals from a human body, the method comprising:

receiving a first light having a wavelength of about 1850 to 1920 nm from a first light source by using a light receiver;

receiving a second light having a wavelength of about 2050 to 2130 nm from a second light source by using the light receiver;

dividing received optical signals into the first light and the second light using a timing circuit;

converting the optical signals divided into the first light and the second light by the timing circuit into voltage signals using a current-voltage converter;

amplifying a signal output from the current-voltage converter using a first operational amplifier;

passing a signal of about 0.1 Hz or higher through a high-pass filter from among signals that passed through the first operational amplifier;

passing a signal of about 20 Hz or lower through a low-pass filter from among the signals that passed through the first operational amplifier;

amplifying a signal that passed through the high-pass filter and the low-pass filter using a second operational amplifier; and calculating a glucose level in blood based on amounts of the first light and the second light received by the light receiver and measuring blood glucose based on the calculated glucose level by using a calculator, wherein the calculator calculates the glucose level in the blood based on subtracting a non-zero amount of light absorbed by water in the human body from the amounts of the first light and the second light received by the light receiver.

10. The method of claim 9, wherein the calculator calculates the glucose level in the blood using BloodGlucose= $(X_t1 \times P1)+(Y_t2 \times P2)+P3$ by combining an amount of light X of the first light source received at a predetermined period of time t1 before a current time and an amount of light Y of the second light source received at a predetermined period of time t2 before the current time with unique constants P1, P2, and P3.

11. The method of claim 9, further comprising, after calculating the glucose level in the blood using the calculator:

measuring any one of ECG and PPG using a body information detector; and correcting the glucose level in the blood calculated by the calculator using a value detected by the body information detector.

12. The method of claim 9, further comprising, after calculating the glucose level in the blood using the calculator:

measuring any one of $SpO_2$ and PPG using a body information detector; and correcting the glucose level in the blood calculated by the calculator using a value detected by the body information detector.

13. The method of claim 9, further comprising, after calculating the glucose level in the blood using the calculator:

measuring any one of GSR and body temperature using a body information detector; and correcting the glucose level in the blood calculated by the calculator using a value detected by the body information detector.

14. The method of claim 9, further comprising, after calculating the glucose level in the blood using the calculator:

measuring a breathing pattern using a breathing pattern detector; and correcting the glucose level in the blood calculated by the calculator using a value detected by the breathing pattern detector.

15. A blood glucose measurement method using multiple body signals, the method comprising:

receiving a first light having a wavelength of about 1850 to 1920 nm;

receiving a second light having a wavelength of about 2050 to 2130 nm;

dividing received signals of the first light and the second light into the first light and the second light;

converting the divided signals into voltage signals;

amplifying the voltage signals;

filtering the amplified signals having about 0.1 Hz or higher through a high-pass filter;

filtering the amplified signals having about 20 Hz or lower through a low-pass filter;

amplifying a filtered signal that passed through the high-pass filter and the low-pass filter;

subtracting a non-zero amount of light absorbed by water in a human body from amounts of the first light and the second light;

calculating a glucose level in blood using BloodGlucose= $(X_t1 \times P1)+(Y_t2 \times P2)+P3$ by combining the amount of light X of the first light received at a predetermined period of time t1 before a current time and the amount of light Y of the second light received at a predetermined period of time t2 before the current time with unique constants P1, P2, and P3;

measuring any one of ECG, PPG, $SpO_2$, GSR, and body temperature;

measuring a breathing pattern; and correcting the calculated glucose level in the blood using the measured values of the ECG, PPG, $SpO_2$, GSR, or body temperature and the breathing pattern.

* * * * *